United States Patent [19]

Cohen et al.

[11] Patent Number: 4,639,775

[45] Date of Patent: Jan. 27, 1987

[54] METHOD FOR DETECTING BLEMISHES NEAR THE PERIMETER OF A CCD IMAGE

[75] Inventors: Edward Cohen, Lancaster; Clarence M. Weaver, Jr., Reamstown; Robert A. Duschl, Lancaster, all of Pa.

[73] Assignee: RCA Corporation, Princeton, N.J.

[21] Appl. No.: 735,054

[22] Filed: May 17, 1985

[51] Int. Cl.[4] .............................................. H04N 7/18
[52] U.S. Cl. ..................................... 358/106; 358/139; 358/213
[58] Field of Search ............... 358/212, 213, 209, 106, 358/139, 163, 10; 382/8

[56] References Cited

U.S. PATENT DOCUMENTS

| | | | |
|---|---|---|---|
| 4,379,308 | 4/1983 | Kosmowski et al. | 358/106 |
| 4,454,541 | 6/1984 | Duschl | 358/106 |
| 4,454,545 | 6/1984 | Duschl | 358/213 |
| 4,496,971 | 1/1985 | West et al. | 358/106 |
| 4,575,751 | 3/1986 | Duschl | 358/213 |
| 4,605,960 | 8/1986 | Cohen | 358/106 |

Primary Examiner—Gene Z. Rubinson
Assistant Examiner—Stephen Brinich
Attorney, Agent, or Firm—E. M. Whitacre; D. H. Irlbeck; L. L. Hallacher

[57] ABSTRACT

In a method of detecting blemishes in the proximity of the perimeter of a CCD image, pairs of adjacent pixels in the proximity of the perimeter are sequentially considered. For each pair of adjacent pixels, a plurality of pixels, in a blemish detection pixel pattern extending toward the center of the image are considered. The sum of the four outer pixels in the pixel pattern are compared to the sum of the inner pixels and the variance is compared to selected minimum and maximum differences. When the variance is outside either the minimum or the maximum differences a blemish has been detected. When the difference is within the two differences no blemish has been found. The blemish pattern is moved one pixel toward the center of the image and the process repeated. The difference comparison is repeated for a selected plurality of times and if desired the differences can be changed for some of the comparisons.

19 Claims, 6 Drawing Figures

METHOD FOR DETECTING BLEMISHES NEAR THE PERIMETER OF A CCD IMAGE

BACKGROUND

This invention relates generally to CCD (charge coupled device) imaging and particularly to a method for detecting blemishes in the proximity of the perimeter of an image on a CCD.

U.S. Pat. No. 4,454,545 issued to R. A. Duschl discloses a CCD based inspection system.

U.S. Pat. No. 4,454,541 issued to R. A. Duschl discloses a system and method for detecting blemishes on the screen of a kinescope. Blemishes are detected by comparing the signal level on each CCD pixel with the average of the signals on the immediately adjacent pixels and generating a blemish signal when the difference exceeds a predetermined threshold.

U.S. Pat. No. 4,575,751 "Method and Subsystem for Plotting The Perimeter of an Object" filed Nov. 15, 1983 by R. A. Duschl discloses a system for plotting the perimeter of an image cast onto a CCD. The image pixels immediately adjacent to the perimeter pixels are identified and their addresses held in memory irrespective of the orientation of the image and the size of the image.

U.S. Pat. No. 4,605,960 entitled "Method for Avoiding Identifying Perimeter Variations As Blemishes In A CCD Image" filed Oct. 22, 1984 by Edward Cohen discloses a method which can be used along with the present invention.

U.S. application Ser. No. 663,153 entitled "Method For Detecting Blemishes Near The Perimeter Of A CCD Image" filed Oct. 22, 1984 by Edward Cohen, discloses a method for detecting blemishes contiguous to a perimeter plotted by the system disclosed in R. A. Duschl U.S. Pat. No. 4,575,751.

The above patents and applications are incorporated herein by reference.

The systems described in the above-referenced applications and patents are quite satisfactory for the purposes intended. However, difficulties sometimes arise because in some instances the light which passes through the image in the proximity of the perimeter is substantially lower than that in the center of the image. The method described in applicaton Ser. No. 663,153 detects blemishes which are contiguous with the perimeter of the object being inspected. This method is not effective in detecting blemishes near to, but spaced from, the perimeter. For these reasons, there is a need for a method of detecting blemishes near an image perimeter which is different from the method used in the center of the image. The present invention fulfills this need.

The present invention is cast into the environment of detecting the perimeter of a black matrix on the inside surface of a CRT faceplate panel. This environment was selected when describing the present invention because the invention is used along with the inventions described in the referenced patents and patent applications and those inventions are described in that environment. Nevertheless it will be understood by those skilled in the art that the present invention is useful in detecting blemishes in the proximity of the perimeter of any image cast onto a CCD.

SUMMARY

A method for detecting blemishes near the perimeter of a CCD (charge coupled device) image the perimeter of which is identified by perimeter identifying pixels which are sequentially considered in a selected direction around the perimeter, includes the steps of defining the consideration of adjacent perimeter identifying pixels as pixel motions, and defining adjacent pixels as pixels having contiguous sides or contiguous corners. A pixel direction matrix is defined wherein the pixel under consideration is surrounded by adjacent pixels whereby side contiguous pixels result in straight pixel motions and corner contiguous pixels result in diagonal pixel motions. Blemish detection motions are defined as motions normal to the straight pixel motions toward the center of the CCD image. Adjacent perimeter identifying pixels are sequentially considered to detect straight and diagonal pixel motions. Blemish detection motions are taken from each of the adjacent perimeter identifying pixels while a plurlaity of pixels along the blemish detection motions are considered. A first portion of the plurality of pixels is compared with a second portion of the pixels and a blemish signal is provided when the comparison results in a variance outside a selected variance range.

DETAILED DESCRIPTION

Figure 1:
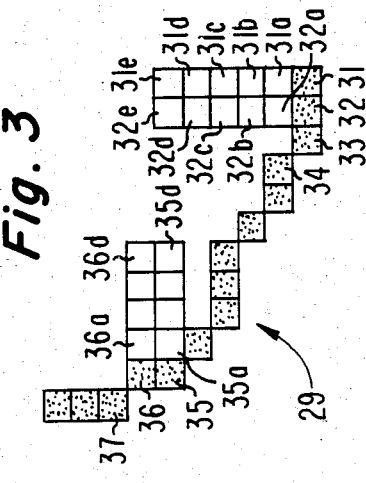
FIG. 1 shows the perimeter of the black matrix present on the inside surface of a faceplate panel.

In FIG. 1, the inside surface of a CRT faceplate panel 11 includes a black matrix which is composed of a plurality of parallel black lines 12 and a perimeter 13. The parallel lines 12 extend across the entire surface of the panel 11 and only several are shown for simplicity. Phosphors are arranged in the spaces between the matrix lines 12 in a sequential fashion and each phosphor emits a different color of light when impacted with electrons. Thus, the phosphors are arranged in a repetitive pattern such as red, green and blue across the entire inside surface of the panel 11 to form a screen 14.

Figure 2:
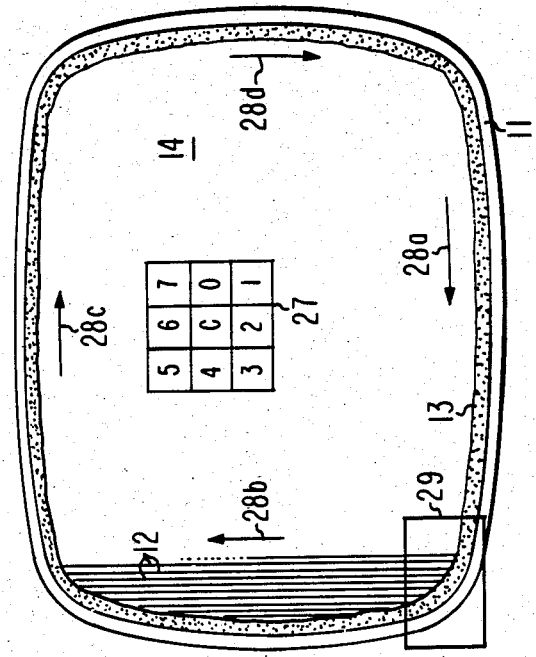
FIG. 2 is a simplified showing of a CCD based image inspection system.

FIG. 2 shows a CCD based inspection system 15 which can be of the type described in U.S. Pat. No. 4,454,545. The inspection system 15 includes a light source 16 the light rays 17 from which fully illuminate the phosphor screen 14 on the inside surface of the panel 11. The light rays 17 pass through the phosphor screen and are focused by a lens 18 onto the CCD 19 within a CCD camera 21. Each pixel, or light sensitive area, of the CCD 19 in the camera 21 is charged to a particular level depending upon the amount of light received by the individual pixels. Thus, the pixels receiving light passing through the screen 14 are charged to a different level than the pixels shaded by the perimeter 13. The pixel data are transferred from the CCD 19 to a central processing unit 22 and processed in accordance with the inspection being made. The inspection can be the detection of blemishes in the screen 14 as described in U.S. Pat. No. 4,454,545 while utilizing the perimeter plotting described in U.S. Pat. No. 4,575,751. The detection of blemishes in the proximity of the perimeter 13 described in the above-referenced U.S. application Ser. No. 663,153 and the method described hereinafter also are carried out in the CPU 22.

Figure 4:
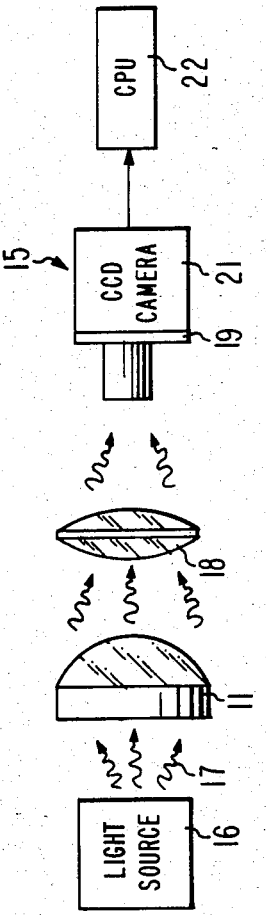
FIG. 4 shows how light intensity decreases in the proximity of the perimeter.

In the blemish detection system described in U.S. Pat. No. 4,454,545 blemishes are detected by comparing the charge level on each CCD pixel with the average of the charges on the eight immediately adjacent pixels. A blemish signal is generated when the difference exceeds a predetermined thereshold. This technique for blemish detection is quite satisfactory in the center of the panel where the intensity of the light passing through the panel is relatively uniform. However, the light intensity drops off sharply as the perimeter 13 (FIG. 1) is approached. Thus, as shown in FIG. 4, the light intensity pattern 23 passing through the panel drops off sharply as the distance from the perimeter 13 decreases. For this reason, a different comparison technique is required in the vicinity of the perimeter 13. In FIG. 4, the spike 24 shows the substantial decrease of light intensity transmitted through the panel 14 which occurs when a dark blemish is detected. Similary, the spike 26 indicates the substantial increase of intensity passing through the panel 14 when a light blemish is detected.

Figure 3:
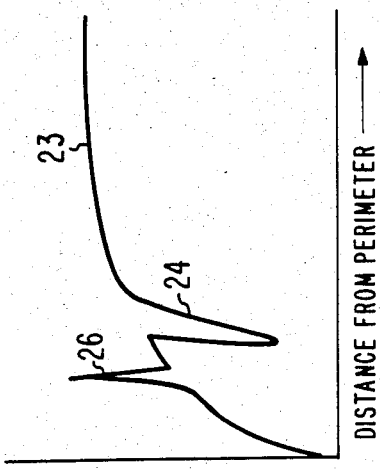
FIG. 3 is an enlarged portion of the black matrix perimeter of FIG. 1 showing how blemish detection motions are turned at the corners of the perimeter.

In FIG. 1, a pixel direction matrix 27 includes a centered pixel C surrounded by eight immediately adjacent pixels identified 0 through 7. When using the present invention, every pixel identified as a perimeter bordering pixel by the perimeter plotting system described in U.S. Pat. No. 4,575,751 is sequentially utilized as the center pixel C of the matrix 27. Accordingly the present invention is useful in conjucntion with the perimeter plotting system. The sequential pixel consideration progresses around the perimeter 13 in a chosen direction, such as clockwise as indicated by the arrows 28a, 28b, 28c and 28d. Obviously, counterclockwise pixel consideration can also be used. Accordingly, while progressing around the perimeter 13, the direction of consideration, with respect to the horizontal and vertical axis of the image, changes periodically. The matrix 27 defines straight and diagonal pixel motions. A straight pixel motion occurs when the pixel adjacent to the center pixel C is pixel 0, 2, 4 or 6. A diagonal pixel motion occurs when the pixel adjacent to the center pixel C is pixel 1, 3, 5 or 7. A straight pixel motion from center pixel C to pixel 4 defines a horizontal-left pixel motion, as indicated by the arrow 28a. The arrow 28b indicates a vertical-up progression, and is a straight pixel motion from center pixel C to pixel 6 of the matrix 27. The arrow 28c indicates a horizontal-right motion and is the consideration of center pixel C and then pixel 0. The arrow 28d indicates a vertical-down motion and is the consideration of center pixel C to pixel 2. The majority of the pixel motions will be straight pixel motions when the consideration occurs in the central portions of the sides of the perimeter 13. However, when a corner is approached, a substantial number of the pixel motions will be diagonal and ultimately a need to change from a horizontal to a vertical direction, or from a vertical to a horizontal direction, occurs. FIG. 3 is an enlarged view of the blocked area 29 of FIG. 1 and shows how changes in direction are effected.

In FIG. 3 the shaded pixels represent the pixels defined as perimeter bordering pixels by the perimeter plotting system described in U.S. Pat. No. 4,575,751.

Assuming that pixel 32 is the first pixel encountered in the blemish detection routine, this pixel is then the center pixel C in the matrix 27 of FIG. 1. When the pixel consideration is in the horizontal-left direction, indicated by arrow 28a, pixel 31 is the adjacent pixel and in accordance with matrix 27 is in the 0 position. Blemish detection motions are defined as motions normal to straight pixel motions, and toward the center of the CCD image. Pixels 31 and 32 are the adjacent pixels under consideration and therefore the blemish detection motion is toward the 6 position of the matrix 27 in FIG. 1. Pixels 31a to 31d and 32a to 32d form the first blemish detection pixel pattern utilized to identify a blemish. The signal levels on these eight pixels are detected. The levels on pixels 31a, 32a, 31d and 32d are added and compared to the total level on the pixels 31b, 31c, 32b, and 32c. The variance between the middle four pixels and the outer four pixels is calculated and compared to maximum and minimum differences. When the variance is below the minimum difference, or above the maximum difference, a blemish has been detected and a blemish signal is given. When the variance is between the maximum and minimum differences no blemish has been detected. In either event, the comparison is repeated fo another blemish detection pattern including a plurality of pixels along the same blemish detection motion. Thus, for the second comparison pixels 31b to 31e and 32b to 32e are considered. Again, the sum of the inner four pixels is compared to the sum of the outer four pixels and the variance compared to the minimum and maximum differences to determine whether or not a blemish has been detected. The comparison is repeated a number of times, for example eight, irrespective of whether or not a blemish is detected. The maximum and minimum differences and the variance between them can be changed for some of the comparisons.

The slope of the intensity pattern 23 in FIG. 4 is very steep in the immediate proximity of the perimeter and flattens out as the center of the CCD image is approached. Accordingly, during the first comparison the variance between the minimum and maximum differences, is rather wide to accommodate the steep slope of the intensity pattern. For the second and subsequent comparisons, the minimum and maximum differences and the variance between them, are changed to accommodate the decrease in the intensity pattern slope. The minimum and maximum differences, and the variance between them, is changed for each comparison until the flat portion of the intensity pattern 23 is reached, after which the differences and the variance are held constant for the remainder of the comparisons. In the preferred embodiment eight comparisons are made along each blemish detection motion and changes are made in the minimum and maximum differences and in the variance for the first four comparisons. These numbers can be changed depending upon the shape of the intensity pattern and the characteristics of the object being inspected.

Minimum and maximum differences are used in calculating the variance for several reasons. First, the calculation is made using levels from a plurality of pixels and therefore an average is obtained. This average does not necessarily fall directly on the intensity pattern and therefore a difference is typical. Also, the use of differences accommodates variations in light transmission through the object being inspected and other characteristics of the system, and such variations are greater in the proximity of the perimeter 13. In the preferred embodiment, and using an intensity pattern similar to that of FIG. 4, the maximum difference is selected in accordance with the substantial variations in light transmission which occur in the proximity of the perimeter 13. The minimum difference is set in accordance with the more uniform conditions nearer to the flat portion of the intensity pattern. As the center of the image is approached the minimum difference is decreased less than the maximum difference, and the variance between the differences is also decreased. Thus, when the first pixel considered is in the closest proximity to the perimeter 13 the maximum difference is set relatively wide because large inherent variations occur in this area and also because one or two of the outer pixels can fall on the perimeter 13. Similarly, the minimum difference is set relatively narrow because random variations are less frequent in this portion of the intensity pattern.

In the preferred embodiment, for the second comparison the maximum difference is decreased, and the minimum difference is held constant. The variance between the minimum and maximum differences therefore inherently increases for the second comparison. For the third and fourth comparisons both differences are decreased but the maximum difference decrease exceeds that of the minimum difference. The variance, therefore, also decreases. For the subsequent comparisons the differences, and the variance are held constant. The level and the slope of the intensity pattern 23 are determined by the light source utilized to illuminate the object being investigated, and by the light transmission characteristics of the object. Accordingly, the values of the differences, the variance between the differences, and the number of needed changes are dictated by these characteristics and the selection of the values, variance and changes are within the purview of one skilled in the art.

After eight comparisons have been completed the investigation advances one pixel along the perimeter. Pixel 33 then becomes the center pixel C of the matrix 27 and pixel 32 is the adjacent pixel. The pixel motion is a straight pixel motion in the 0 direction, and the blemish detection motion remains the 6 direction. The procedure of utilizing pixel detection patterns including eight pixels, to calculate variances for comparison with various minimum and maximum differences is repeated for the selected number of comparisons. Pixel 34 becomes the next center pixel C of matrix 27 and pixel 33 is the adjacent pixel. In matrix 27, this is a diagonal pixel motion in the 1 direction. However, the diagonal direction of the pixel motion is ignored and the threshold comparisons are made in the existing 6 direction. The investigation continues with the blemish detection motions in the 6 direction until a 90° change in the straight pixel motion occurs. Accordingly, when pixel 36 becomes the center pixel C of matrix 27, pixel 35 is the adjacent pixel. The pixel motion then is straight in the vertical-up direction and, thus, is a 2 direction motion. Accordingly, the blemish detection motion meeting the criteria of being toward the center of the image, and normal to the pixel motion, is the 0 direction motion. The first comparison is therefore made utilizing pixels 35a to 35d and 36a to 36d. The other comparisons also are made on pixels aligned with pixels 35 and 36. For the next set of comparisons pixel 37 is the center pixel C of and pixel 36 is the adjacent pixel. In matrix 27, this is a diagonal 1 motion. Nevertheless, the comparisons are made in the 0 direction because a need for a turn in direction has not been indicated by a 90° change in the pixel motion direction. The sequential consideration of the pixels defining the border 13 continues in the vertical up direction indicated by arrow 28b until the upper left hand corner of the perimeter is reached and the direction changes to horizontal-right indicated by the arrow 28c. The blemish detection motions are then made in 2 direction. The sequential investigation of the perimeter bordering pixels continues around the perimeter until all pixels are utilized as center pixel C in matrix 27.

Figure 5A:
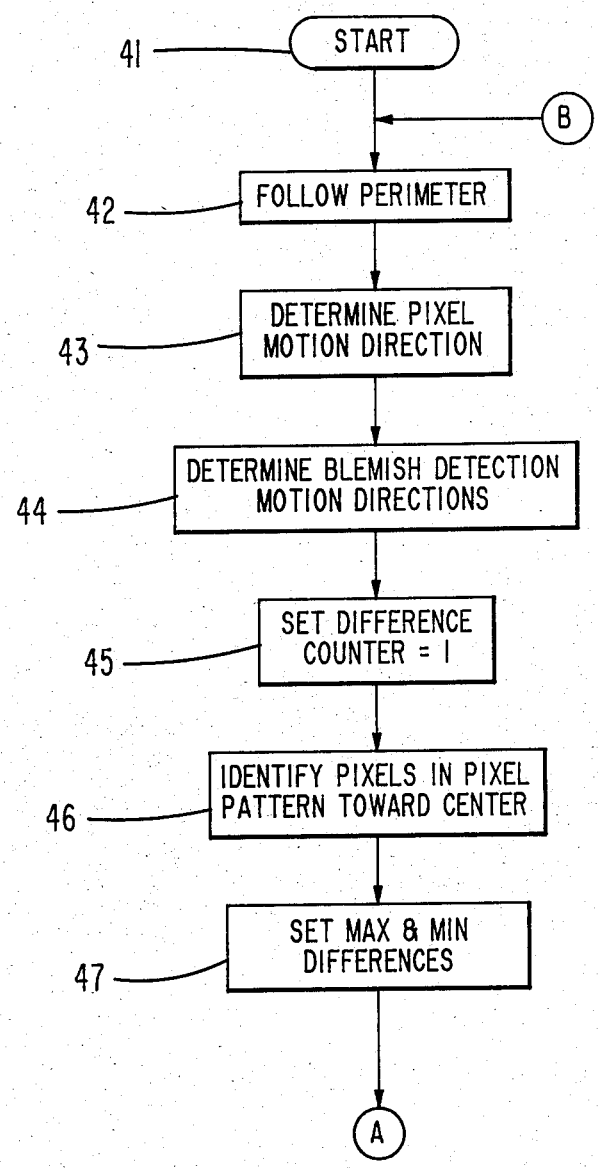
FIGS. 5a and 5b are a flow chart of a preferred embodiment.
Figure 5B:
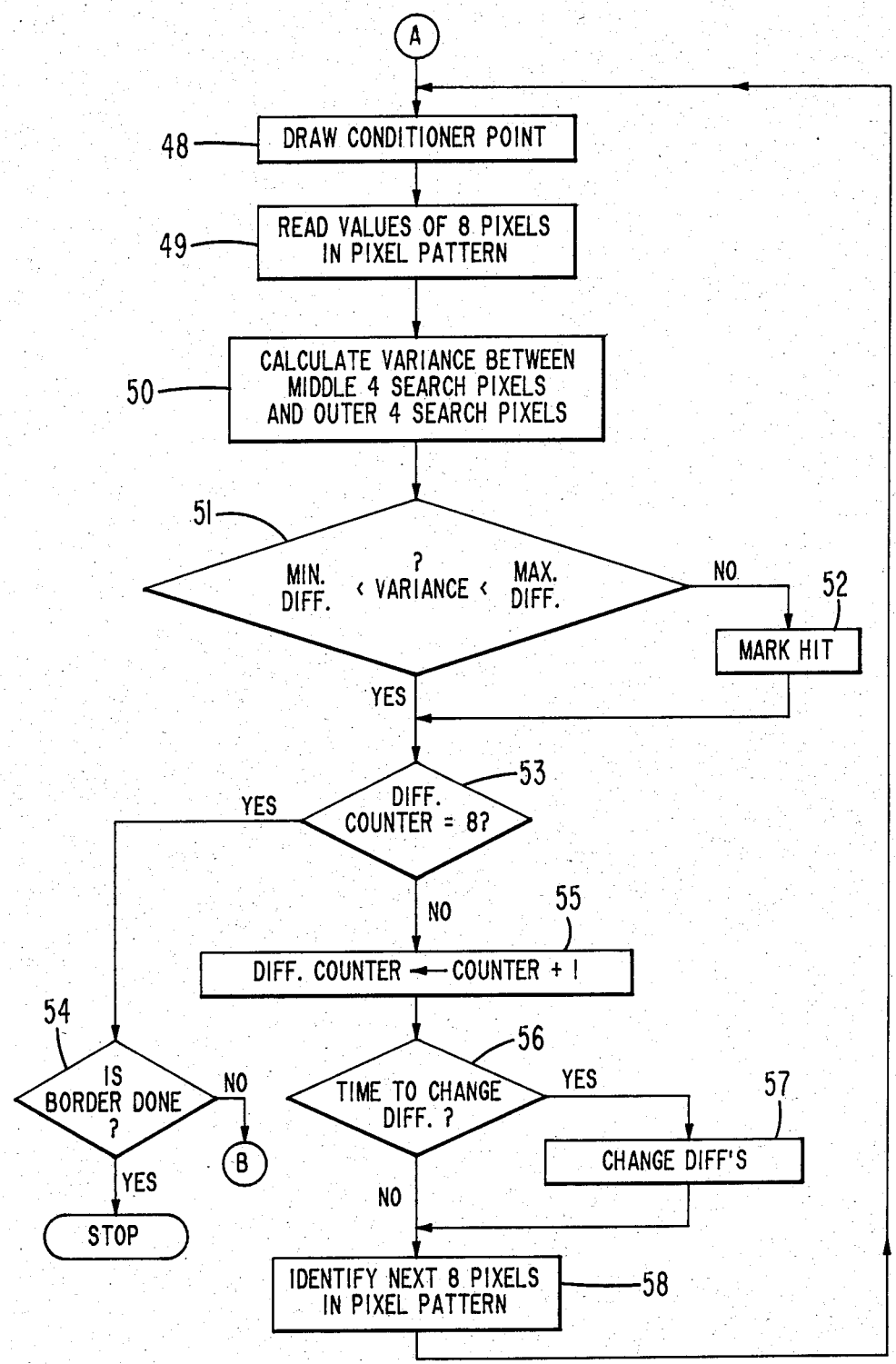

FIGS. 5a and 5b are a flow chart of a preferred embodiment. In FIG. 5a, the near perimeter blemish detection begins at start 41. Step 42 is entered to follow the perimeter 13 (FIG. 1). The perimeter preferrably is followed in the manner fully described in U.S. Pat. No. 4,575,751. Step 43 is entered to determine the pixel motion direction. This direction is determiend by the pixel under consideration and the adjacent pixel in the perimeter 13 in accordance with matrix 27 of FIG. 1. Step 44 is entered to determine the blemish motion direction. This, also, is consistent with the pixel matrix 27 of FIG. 1 and identifies whether the blemish detection motions are to be taken in the 0, 2, 4, or 6 direction of the matrix. Step 45 is entered to set the difference counter to one. At step 46 the eight pixels in the pixel pattern, such as pixels 31a to 31d and 32a to 32d of FIG. 3, are identified. After the eight pixels in the pixel pattern are identified step 47 is entered to set the minimum and maximum differences into the system. The differences and the variance between the differences are determiend by the intensity pattern 23 in FIG. 4, as explained hereinabove.

Step 48 of FIG. 5b is entered to draw the conditioner point to verify that the invention described herein must be used. This step is used to verify that the pixels in the blemish detection pixel pattern, which are closest to the perimeter 13, are sufficiently close to the perimeter to warrant utilizing the near perimeter detection routine described herein. As stated hereinabove, for pixels in the proximity of the center of the image, that is, those along the flatter portion of the intensity pattern 23 of FIG. 4, the blemish detection routine described in U.S. Pat. No. 4,454,545, is used to identify blemishes. Accordingly, because a plurality of comparisons (eight)is made for each pair of adjacent pixels and because each comparison moves four pixels toward the image center, the present invention detects blemishes that begin within the first eleven pixels of the perimeter 13. However, blemishes which begin within the first eleven pixels, but which do not have a portion within the first eight pixels of the perimeter, can also be identified by the system described in U.S. Pat. No. 4,454,545. "The conditioner point thus, shows that the pixels being considered fall within the first eleven pixels from the perimeter.

At step 49 the charge levels on the eight pixels in the blemish detection pixel pattern are read. Step 50 is then entered to calculate the variance between the four middle pixels and the four outer pixels. In FIG. 3, the variance between the sum of the four middle pixels 31b, 31c, 32b, 32c and the sum of the four outer pixels 31a, 31d and 32a, 32d is calculated. Decision step 51 is entered to determine whether or not the variance calculated in step 50 is between the minimum and maximum differences set into the system at step 47. When the variance is not between the differences step 52 is entered to identify that a blemish has been detected. When the variance is between the differences step 53 is entered to determine whether the difference counter reads eight. When eight difference comparisons have been made step 54 is entered to determine whether or not the complete perimeter has been investigated. If the complete perimeter has been investigated the investigation is stopped. If the complete perimeter has not been investigated step 42 is re-entered and the previous center pixel C is incremented to the adjacent pixel of matrix 27 and the next pixel becomes the center pixel. Thus, in FIG. 3 when the first two pixels considered are 31 and 32 upon re-entering step 47 the two adjacent pixels become 32 and 33. In step 53, when the difference counter shows that eight comparisons have not been completed step 55 is entered to increment the counter one count and step 56 is entered to determine whether or not the differences should be changed. Irrespective of whether or not the differences are changed, step 58 is entered to identify the next 8 pixels, and step 48 is re-entered to repeat the comparison process.

What is claimed is:

1. A method for detecting blemishes near the perimeter of a CCD (charge coupled device) image, wherein said perimeter is identified by perimeter identifying CCD pixels, and wherein said perimeter identifying pixels are sequentially considered in a selected direction around said perimeter, said method comprising the steps of:

detecting the charge levels of perimeter identifying pixels in a sequence of pixel motions, wherein a pixel motion is the detection of adjacent pixel charge levels and wherein adjacent pixels are pixels having contiguous sides or contiguous corners, said pixel motions being taken in directions defined by a pixel direction matrix wherein the pixel being detected is surrounded by adjacent pixels whereby the detection of side adjacent pixels results in straight pixel motions and the detection or corner adjacent pixels results in diagonal pixel motions, and whereby blemish detection motions are motions normal to said straight pixel motions toward the center of said CCD image;

sequentially detecting the charge levels on adjacent perimeter identifying pixels to detect straight and diagonal pixel motions;

taking blemish detection motions from each of said adjacent perimeter identifying pixels while considering a plurality of pixels along said blemish detection motions; and comparing a first portion of said plurality of pixels with a second portion of said pixels and providing a blemish signal when the comparison is outside a selected variance.

2. The method of claim 1 wherein said first portion of pixels are the pixels closest to, and furthermost from, said perimeter, and said second portion of pixels are the remaining pixels.

3. The method of claim 2 wherein said straight pixel motions are horizontal left, vertical up, horizontal right, and vertical down; and further including the step of turning said blemish detection motion 90° when said sequential consideration of pixels changes from one of said straight pixel motions to another of said straight pixel motions.

4. The method of claim 3 wherein said plurality of pixels includes two adjacent perimeter identifying pixels, and at least eight pixels aligned with each of said adjacent perimeter identifying pixels along said blemish detection motions.

5. The method of claim 4 further including the step of shifting said plurality of pixels one pixel away from said perimeter, along a blemish detection motion, and repeating said comparison for the same number of pixels; and also including the step of repeating said shifting and said comparison a plurality of times.

6. The method of claim 5 including the step of changing said range for at least one of said shifts of said comparisons.

7. The method of claim 6 wherein said plurality of pixels is shifted seven times.

8. The method of claim 7 wherein said variance is tightened for at least the first three of said shifts.

9. The method of claim 8 wherein said pixel under consideration is adjaent to eight pixels whereby four straight pixel directions and four diagonal pixel directions are defined.

10. The method of Claim 9 wherein said pixel under consideration is sequentially moved along said perimeter identifying pixels and said pixel direction matrix follows said pixel under consideration.

11. The method of Claim 9 further including the step of drawing a conditioner point to verify that the pixels in said pixel pattern are within a preselected number of pixels to said perimeter.

12. The method of claim 5 further including the step of drawing a conditioner point to verify that the pixels in said pixel pattern are within a preselected number of pixels to said perimeter.

13. The method of claim 5 further including the step of selecting a maximum charge level difference and a minimum charge level difference and providing a blemish signal when said variance exceeds said maximum difference or is less than said minimum difference.

14. The method of claim 13 further including the step of changing at least one of said differences for at least one of said comparisons.

15. The method of claim 14 including the step of changing said variance for at least one of said shifts of said comparisons.

16. The method of claim 3 further including the step of drawing a conditioner point to verify that the pixels in said pixel pattern are within a preselected number of pixels to said perimeter.

17. The method of claim 1 further including the step of selecting a maximum charge level difference and a minimum charge level difference and providing a blemish signal when said variance exceeds said maximum difference or is less than said minimum difference.

18. The method of claim 17 further including the step of changing at least one of said differences for at least one of said comparisons.

19. The method of claim 18 including the step of changing said variance for at least one of said shifts of said comparisons.

* * * * *